(12) United States Patent
Jerome et al.

(10) Patent No.: US 8,772,526 B2
(45) Date of Patent: Jul. 8, 2014

(54) METHOD FOR PREPARING DITHIOCARBAMATES IN PARTICULAR FROM POLYOLS OF THE GLYCEROL TYPE

(75) Inventors: Francois Jerome, Sevres Anxaumont (FR); Rodolphe De Sousa, Migne-Auxances (FR); Joel Barrault, Liguge (FR); Yannick Pouilloux, Mignaloux-Beauvoir (FR)

(73) Assignees: Centre National de la Recherche Scientifique, Paris (FR); Universite de Poitiers, Poitiers (FR)

( * ) Notice: Subject to any disclaimer, the term of this patent is extended or adjusted under 35 U.S.C. 154(b) by 0 days.

(21) Appl. No.: 13/517,335

(22) PCT Filed: Dec. 21, 2010

(86) PCT No.: PCT/FR2010/052867
§ 371 (c)(1),
(2), (4) Date: Jul. 5, 2012

(87) PCT Pub. No.: WO2011/083255
PCT Pub. Date: Jul. 14, 2011

(65) Prior Publication Data
US 2012/0264941 A1 Oct. 18, 2012

(30) Foreign Application Priority Data
Dec. 21, 2009 (FR) .................................. 09 06203

(51) Int. Cl.
*C07C 333/00* (2006.01)
(52) U.S. Cl.
USPC .......................................... 558/236; 558/237

(58) Field of Classification Search
USPC .................................................. 558/237, 236
See application file for complete search history.

(56) References Cited

U.S. PATENT DOCUMENTS 3,407,222 A 10/1968 Lies

OTHER PUBLICATIONS

Len, C. et al., "Synthesis of carbamic esters derivatives of itols: antifungal activity against various crop diseases," Journal of Agricultural and Food Chemistry, Jan. 20, 1997, vol. 45, No. 1, pp. 3-6.

*Primary Examiner* — Nizal Chandrakumar
(74) *Attorney, Agent, or Firm* — Birch, Stewart, Kolasch & Birch, LLP

(57) ABSTRACT

The present invention concerns a method for the synthesis of glycerol dithiocarbamates or bis-dithiocarbamates (GDTCs) in which a reaction medium comprising (1) a carbonate selected from diethyl carbonate, dimethyl carbonate and ethylene or propylene carbonate associated with a glycerol type polyol in the presence of a basic catalyst or (2) a cyclic carbonate comprising five ring members, in a solvent medium, is supplemented with a primary or secondary amine in the presence of carbon disulphide, and the GDTC formed is recovered. In particular, a glycerol type polyol is brought into the presence of diethyl carbonate in the presence of a catalyst, then a primary or secondary amine is added to the reaction medium in the presence of carbon disulphide, and the GDTC formed is recovered. The invention can be used for one-step synthesis of glycerol dithiocarbamates directly from glycerol as the starting material and solvent. This method involves glycerol, diethyl carbonate, carbon disulphide ($CS_2$) and a primary or secondary amine to produce glycerol dithiocarbamates; the glycerol/NaOH phase can be recycled 6 times without a noticeable drop in yield; the ethyl acetate is also recycled after each extraction.

19 Claims, 1 Drawing Sheet

METHOD FOR PREPARING DITHIOCARBAMATES IN PARTICULAR FROM POLYOLS OF THE GLYCEROL TYPE

This application is the National Phase under 35 U.S.C. §371 of International Application No. PCT/FR2010/052867 with and international filing date of Dec. 21, 2010, which claims priority to 09/06203 filed in France on Dec. 21, 2009. The entire contents of all applications are incorporated herein by reference.

The present invention relates to a novel method for preparing dithiocarbamates, and to their uses, in particular in the phytosanitary field.

FIELD OF THE INVENTION

Dithiocarbamates constitute a broad chemical family and are used in rubber chemistry, as vulcanization accelerators or to control radical polymerizations, as enzyme inhibitors having major effects on many biological systems, and in the phytosanitary and pharmaceutical fields. The dithiocarbamic acid derivative family in particular includes derivatives of zinc, iron, sodium and manganese used as pesticides and/or dithiocarbamates soluble in water and also means that the inappropriate use of metals can be avoided.

Glycerol dithiocarbamates or glycerols functionalized with a dithiocarbamate function are of particular interest since they are more biocompatible and biological tests demonstrate that they have pesticidal properties. Thus, certain glycerol dithiocarbamates (GDTCs) have been shown to be promoters, according to some studies[1 to 4], with antifungal properties close to those of maneb and the sodium salt of diethyldithiocarbamic acid. Certain GDTCs are used in medicine for the treatment of cancers. The GDTC family is also a family of molecules that are important in trapping metals.

They are usually synthesized using conventional organic chemistry pathways, in a plurality of steps, producing a great deal of waste and in generally poor yields.

PRIOR ART

Such molecules are generally synthesized in the form of salts which provide for their solubility in water, in accordance with scheme 1 below, by substituting the metal with a natural polyol (A) or by conventional pathways starting from synthetic products (B).

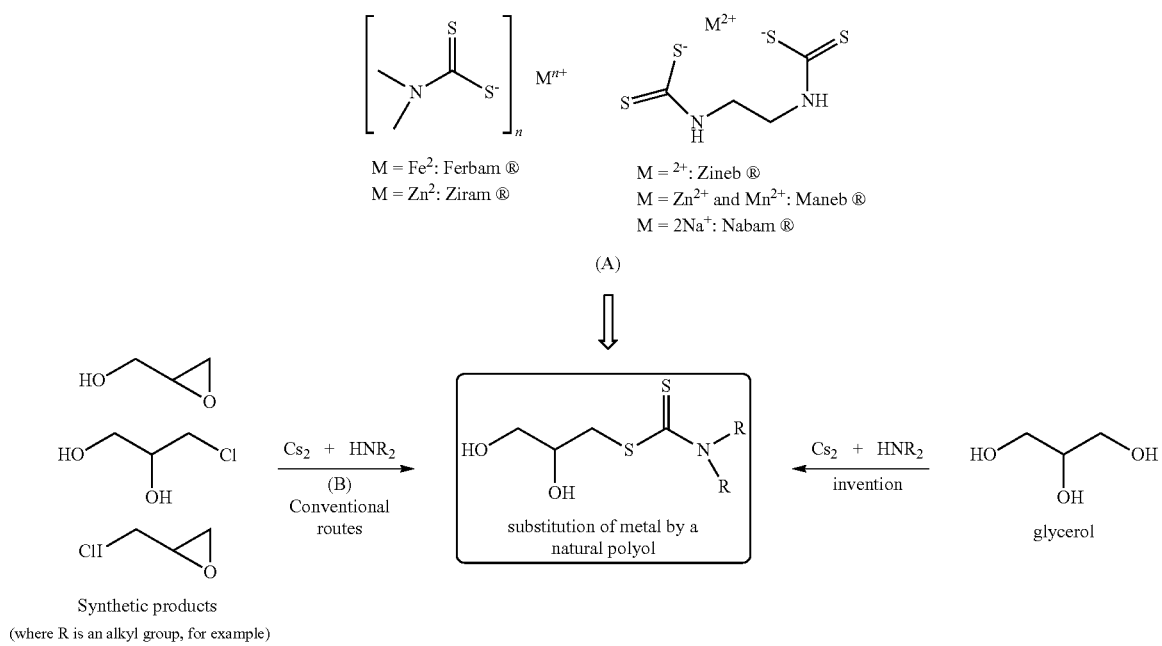

Scheme 1 fungicides, for market gardening or for the cultivation of cereals or vines, for example. However, toxicological problems (associated diseases) and environmental problems, such as ground and water table contamination, arise from the intensive use of such pesticides, which are toxic and of low biodegradeability. Their metabolization can liberate highly toxic compounds, in particular ethylene thiourea, which is recognized as a being responsible for cancers of the thyroid and Parkinson's disease. Because of their toxicity and that of their metabolites, interest has arisen in substituting the metals with polyols, in particular natural polyols such as glycerol and sugars. Forming dithiocarbamate derivatives with hydrocarbon molecules, in particular with polyols[1 to 6], renders the From the point of view of synthesis, directly introducing dithiocarbamate onto glycerol is complicated. The nucleophilic substitution of one of the hydroxy groups of the glycerol is difficult and it is generally preferable to use alkyl halides rather than alcohols, but such pathways produce a stoichiometric quantity of salt.

Using a method involving alcohols and a Mitsunobu reagent is known, and that generates a stoichiometric quantity of waste. In addition, starting from glycerol, which includes three hydroxy groups, means that polysubstituted products are formed and so protective and deprotection agents have to be employed, something that makes purification complex.

For these reasons, natural glycerol is not used for the production of GDTCs, but rather more reactive compounds such as glycidol, epichlorhydrin or 3-chloropropane-1,2-diol, using conventional pathways (B) (see scheme 1).

Thus, Ruffin et al.[1] describe the synthesis of carbamic esters with a hydrocarbon backbone derived from glycerol or D-glucose and two N,N-diethyldithiocarbamoyl groups and of bisdithiocarbamic esters having ketone or alkyl ester functions. Glycerol bis-dithiocarbamates were obtained from 1,3-dichloro-1,3-dideoxyglycerol and lithium salts of N,N-diethyldithiocarbamic acid, in acetone under reflux. Their antifungal activity towards *Fusarium oxysporum* was evaluated and compared with maneb and the sodium salt of N,N-diethyldithiocarbamic acid.

Len et al.[2] described the synthesis of carbamic esters with an itol backbone and one or two thiocarbamoyl groups starting from 2,3-O-isopropylidene-DL-glycerol or 1-chloro-1-deoxyglycerol, and their antifungal activity on *Alternaria brassicae, Pseudocercosporella herpotrichoides, Septoria nodorum* and *Phytophtora cinnamomi*, compared with that of carbendazim and maneb.

Len et al.[3] described a synthesis of glycerol bis-dithiocarbamates starting from 1,3-dichloro-1,3-dideoxyglycerol and lithium salts of N,N-diethyldithiocarbamic acid, in acetone under reflux, and their antifungal activity on the same species, compared with that of carbendazim and maneb.

Len et al.[4] described a four-step synthesis of carbamic esters starting from 1,2-5,6-di-O-isopropylidene-α-D-glucofuranose, as well as their antifungal activity on the same species, compared with that of carbendazim and maneb.

Len et al.[5,6] described the regiospecific bis-carbamoylation of protected D-glucose (di-O-isopropylidene-D-glucose) by a four-step method that used the 3-iodo-6-O-tosylated protected compound.

The document FR 2 735 130 describes the synthesis of polyol dithiocarbamates where epichlorhydrin or 1,3-dichloro-2-propanol, which are expensive and toxic, are reacted with dithiocarbamic salts in the presence of highly environmentally-unfriendly organic solvents (dimethylsulphoxide, toluene). The reaction has low selectivity and generates large quantities of salts; these latter are difficult to eliminate, increasing the economic and environmental costs of the synthesis.

The known syntheses mentioned above use chemical substances which are frequently toxic, expensive and likely to generated a great deal of waste.

Thus, there is a need for a method for synthesizing GDTCs, dithiocarbamate compounds, in particular fungicides and/or pesticides, which can be carried out in a simple manner in a few steps, which method is inexpensive and which has less impact on the environment than the usual methods, and in particular which does not use a harmful organic solvent, which has good yields, good regioselectivity and good chemoselectivity, with by-products that can be readily eliminated or re-used, and which can be carried out starting from cheap, widely available starting products.

The Applicant has now developed a method for the synthesis of glycerol dithiocarbamate or bis-dithiocarbamates (hereinafter GDTCs) in which a reaction medium comprising (1) a carbonate selected from diethyl carbonate, dimethyl carbonate, ethylene carbonate and propylene carbonate, associated with a glycerol type polyol in the presence of a basic catalyst or (2) a cyclic carbonate comprising five ring members, in a solvent medium, is supplemented with a primary or secondary amine in the presence of carbon disulphide, and the GDTC formed is recovered.

In a first implementation, the invention concerns a method for the preparation of glycerol dithiocarbamates (GDTCs) in which a glycerol type polyol is brought into the presence of a carbonate selected from diethyl carbonate, dimethyl carbonate, ethylene carbonate and propylene carbonate, in the presence of a basic catalyst, then a primary or secondary amine is added to the reaction medium in the presence of carbon disulphide, and the GDTC formed is recovered.

In a second implementation, a cyclic carbonate comprising five ring members, in a solvent medium, is reacted with a primary or secondary amine, meaning that the GDTCs are obtained in a single step. The advantages of this variation include the very high purity of the GDTCs obtained as well as very high yields.

The synthesis pathways of the invention differ from those described in FR 2 735 130 and the articles cited above in the synthesis strategy used and in the substrates employed. The method of the present invention has the following advantages, inter alia. With the invention, it is now possible to synthesize GDTCs under particularly mild conditions and in a highly selective manner by substituting a hydroxy group of the glycerol or a glycerol type polyol with a dithiocarbamate group. This synthesis pathway is consistent with the concept of "green chemistry". It is economic with atoms and produces little or no sulphur-containing or nitrogen-containing waste and neither metals nor salts.

It concerns the synthesis of various GDTCs in a single step, directly from glycerol, a natural derivative, which is non-toxic, widely available, biodegradable and not expensive, and even from other glycerol type polyols, in particular from other diols, associated with a carbonate or even directly from carbonates comprising five ring members. In fact, the synthesis pathway is not limited to glycerol alone: other polyols comprising the motif —CH(OH)—CH$_2$OH, such as propanediol or ethylene glycol, may be coupled to a carbonate, an amine and to carbon disulphide to produce the corresponding dithiocarbamate esters. Carbonates comprising five ring members, in the presence of an amine and carbon disulphide, also result directly in the corresponding GDTCs.

The invention opens up the way to syntheses which in particular have the following advantages—they are environmentally protective and economically viable, since the starting products are cheap and widely available such as glycerol, which is co-product of the vegetable oil industry and the biodiesel industry, and are converted into products with a high added value. The synthesized products may be considered to be products that are safer than pesticides, fungicides or in general the usual phytosanitary products.

In addition, the results of large scale synthesis are in agreement with the results obtained in the laboratory.

The method of the present invention can not only allow the direct introduction, in a single step, of a dithiocarbamate group onto the polyol molecule in accordance with the preferred variation, it can also regioselectively and chemoselectively activate the glycerol, or even other polyols. The method of the invention is an advantageous alternative to enzymatic methods which until now are the only ones that can precisely control the selectivity of reactions involving glycerol in particular.

The present invention also concerns the use of a glycerol type polyol or glycerol as a solvent in a method in accordance with the invention.

As will become apparent from the following detailed description and examples, the method of the invention overcomes the various problems mentioned above. Other advantages and characteristics of the invention will become apparent from the following detailed description and examples made with reference to the accompanying drawings.

Figure 1:
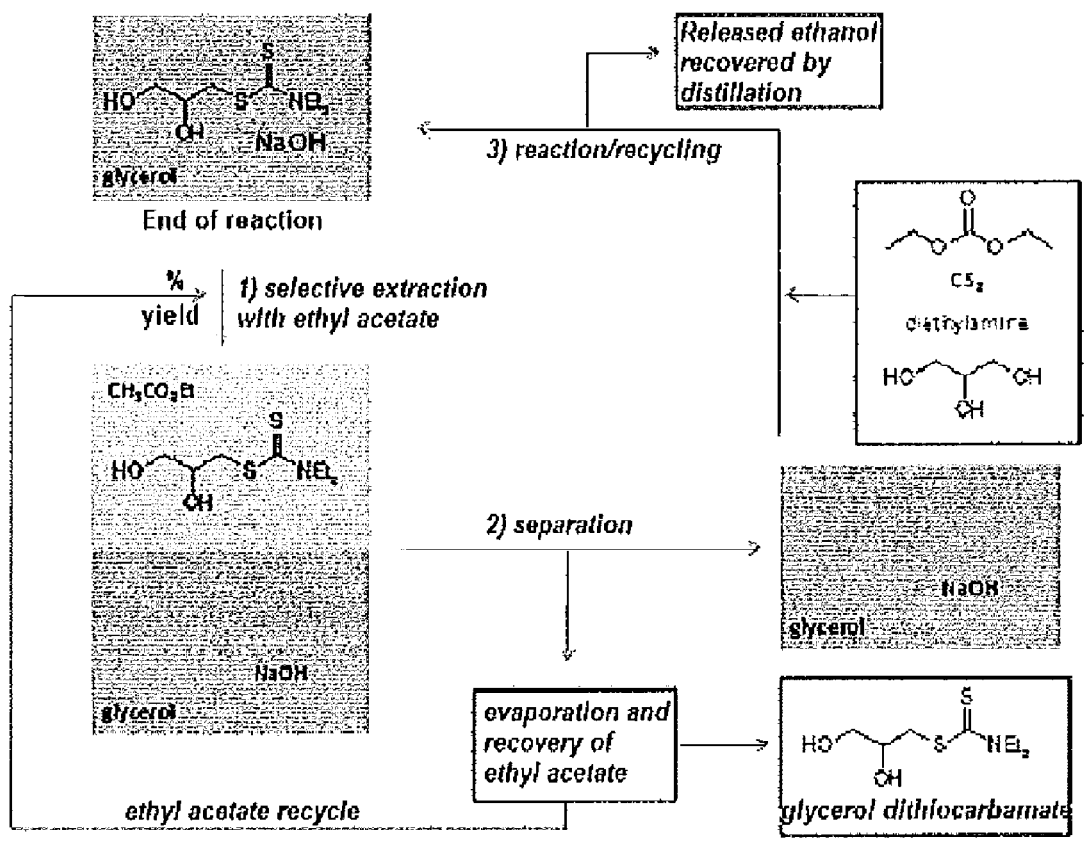
FIG. 1 represents a scheme for a method of the invention carried out in accordance with the first variation, using glycerol and diethyl carbonate, NaOH, $CS_2$ and $NH(C_2H_5)_2$, and the recycles which are carried out.

Scheme 2 below shows the synthesis pathway of the first variation which comprises carbonation of polyol followed by reaction with the amine and $CS_2$. It is a method known as a "one-pot-two-step" method:

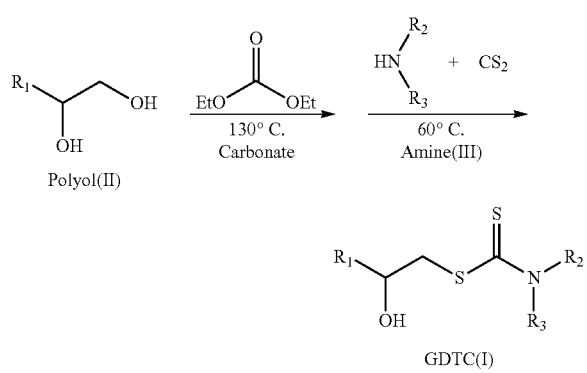

(where $R_1$, $R_2$ and $R_3$ have the meanings given below.)

In the variation illustrated above with diethyl carbonate, the carbonate may also be selected from diethyl carbonate, dimethyl carbonate and ethylene carbonate or propylene carbonate.

However, in a particular implementation, the process may be carried out directly from a cyclic carbonate in accordance with Scheme 3 below:

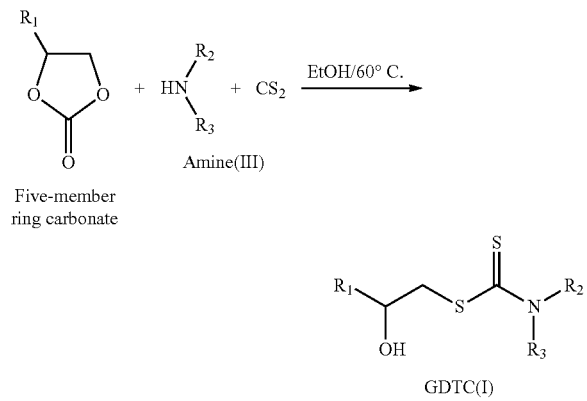

(where $R_1$, $R_2$ and $R_3$ have the meanings given below.)

or a cyclic carbonate comprising five ring members in accordance with scheme 3' below,

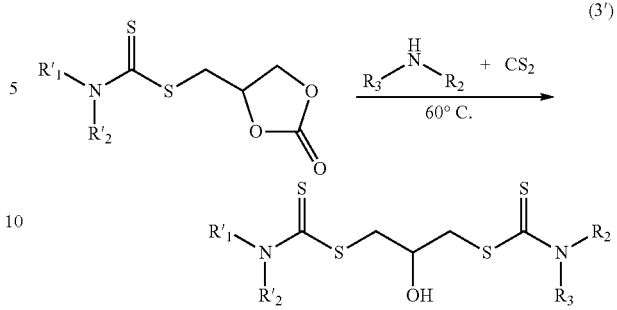

where $R'_1$ and $R'_2$ have the same meanings as $R_2$ and $R_3$, the meanings of which are given below;

or a cyclic polycarbonate comprising five ring members in accordance with scheme 3" below:

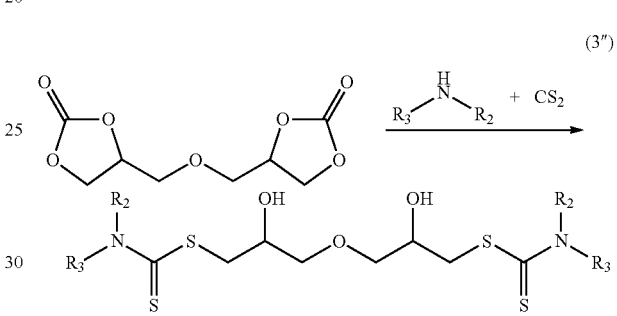

where $R_2$ and $R_3$ have the meanings given below.

More precisely, the invention concerns a method for the preparation of GDTCs with formula (I):

$$R_1-CH(OH)-CH_2-S-C(S)-NR_2R_3 \qquad (I)$$

in which $R_1$ represents H;

a $C_1$-$C_{22}$ alkyl radical, linear or branched or a $C_3$-$C_{16}$ cyclo-alkyl radical, substituted or not substituted with one (or more) hydroxy, —O-alkyl, thiohydroxy or —S-alkyl group(s), the chain of the alkyl radical possibly being interrupted by one or more O, N or S heteroatoms;

a linear or branched, mono- or poly-unsaturated $C_2$-$C_{22}$ alkenyl radical;

a $C_2$-$C_6$ alkynyl radical;

a $C_6$-$C_{10}$ aryl radical; or a $C_7$ to $C_{22}$ arylalkyl radical;

and

—$R_2$ and $R_3$, independently of each other, represent H;

a $C_1$-$C_{22}$ alkyl radical, $C_3$ to $C_{16}$ linear or branched or cyclo-alkyl radical not substituted or substituted with one (or more hydroxy, —O-alkyl, thiohydroxy or —S-alkyl group(s), the chain of the alkyl radical possibly being interrupted by one or more O, N or S heteroatoms;

a linear or branched, mono- or poly-unsaturated $C_2$-$C_{22}$ alkenyl radical;

a $C_2$-$C_6$ alkynyl radical;

a $C_6$-$C_{16}$ aryl radical; or a $C_7$ to $C_{22}$ arylalkyl radical; or $R_2$ and $R_3$ together with the nitrogen atom to which they are bonded form a cycloamino group.

In a particular implementation, it concerns glycerol bis-dithiocarbamate compounds with formula:

or with formula:

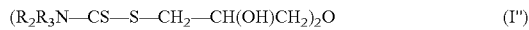

where $R'_1$ and $R'_2$ have the same meanings as $R_2$ and $R_3$ above.

According to this method, in a first variation, the polyol, a carbonate and a basic catalyst are brought together and a primary or secondary amine is added in the presence of $CS_2$.

The term "alkyl" means a linear or branched hydrocarbon chain containing 1 to 22 carbon atoms, preferably 1 to 12 carbon atoms, more preferably 1 to 8 carbon atoms. Particular non-limiting examples of alkyl groups are methyl, ethyl, propyl, isopropyl, butyl, t-butyl, pentyl, hexyl and cyclohexyl.

The term "cycloalkyl" means a saturated carbocyclic system containing 3 to 16, for example 3 to 7 carbon atoms, preferably 5 to 10 carbon atoms, and more preferably 5 to 7 carbon atoms and having 1, 2 or 3 cycles. Non-limiting examples of cycloalkyl groups are cyclopropyl, cyclopentyl, cyclohexyl and cycloheptyl.

The term "alkenyl" means a linear or branched aliphatic hydrocarbon group containing at least one carbon-carbon double bond and 2 to 22 carbon atoms, preferably 2 to 12 carbon atoms, more preferably 2 to 8 carbon atoms. Non-limiting examples of alkenyl groups are: ethenyl, propenyl, n-butenyl, n-pentenyl, octenyl and decenyl.

The term "alkynyl" means a linear or branched aliphatic hydrocarbon group containing at least one carbon-carbon triple bond and 2 to 6 carbon atoms, preferably 2 to 4 carbon atoms. Non-limiting examples of alkynyl groups are: ethynyl, propynyl, 2-butynyl, 3-methylbutynyl and n-pentynyl.

The term "heteroalkyl" in the above alkyls means an alkyl radical as defined above, in which one or more carbon atoms is replaced by a sulphur, oxygen or nitrogen atom.

The term "aryl" means a monocyclic or multicyclic aromatic group system comprising at least one aromatic ring containing 6 to 16 carbon atoms, preferably 6 to 10 carbon atoms. A non-limiting example of an aryl group is phenyl.

The aryl group may or may not be substituted with 1, 2, 3 or 4 substituents selected independently of each other. A non-limiting example of a substituted aryl group is hydroxyphenyl.

In cycloalkyls, when the chain of the cycloalkyl radical is interrupted by one or more heteroatoms, it is termed a "heterocycloalkyl", which means a saturated, monocyclic or multicyclic non-aromatic system containing 3 to 16 (for example 3 to 7) carbon atoms, preferably 5 to 10 carbon atoms, and more preferably 5 to 7 carbon atoms and having 1, 2, 3 or 4 cycles, in which one or more of the atoms of the system is an element other than a carbon atom, such as a sulphur, oxygen and/or nitrogen atom. A preferred example of a heterocycle of the present application is piperidyl.

The term "arylalkyl" or "aralkyl" means an aryl as defined above bonded to an alkyl group as defined above, the bond to the parent group being via the alkyl group. A non-limiting example of an arylalkyl group is benzyl.

The term "heteroaryl" means a system with 5 to 14, preferably 5 to 10 simple or fused aromatic rings, these rings comprising 1, 2 or 3 heteroatoms selected independently of each other from O, S and N, it being understood that the rings do not have adjacent oxygen or sulphur atoms. A preferred heteroaryl group contains 5 or 6 atoms. In a further preferred embodiment, the heteroaryl is monocyclic. The heteroaryl group may or may not be substituted with 1, 2 or 3 substituents selected independently of each other. Non-limiting examples of heteroaryl groups are as follows: pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl and benzothiazolyl. Preferred examples of monocyclic heteroaryls are pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, pyrazinyl and pyridazinyl.

The term "heteroaralkyl" or "heteroarylalkyl" means a heteroaryl group as defined above bonded to an alkyl group as defined above, the bond to the parent group being via the alkyl group.

The term "cycloamino group" means a secondary amino group, a saturated cyclic dialkylamino system containing 3 to 10 (for example 3 to 7) carbon atoms, preferably 4 to 10 carbon atoms, and more preferably 4 to 7 carbon atoms and having 1, 2 or 3 cycles. A non-limiting example of a cycloamino group is the piperidine group.

The term "aminoalkyl" means an alkyl group as defined above, substituted with one or more $NH_2$ groups. A non-limiting example of such a group is the group —$C_2H_4$—$NH_2$.

The term "substituent" means, an ether, a hydroxy, a carboxamide, an ester, a ketone, an aryl, a heteroaryl, a cycloalkyl, an amine, a substituted amine, a linear or branched alkyl, in particular a $C_1$ to $C_6$ alkyl, cyano, a nitro, a haloalkyl, an alkoxy, a carboxyalkyl, a mercapto, a sulphhydryl, an alkylamino, a dialkylamino, a sulphonyl and a sulphonamido group. In one particular implementation, when a heteroaryl is substituted, in particular a monocyclic heteroaryl, the substitution takes place on the heteroatom(s) of the cycle. Alternatively or in combination with the preceding embodiment, when a heteroaryl is substituted, in particular a monocyclic heteroaryl, the substitution takes place on the carbon atom or atoms of the cycle.

In the present invention, the substituents are preferably hydroxy, —O-alkyl, thiohydroxy or —S-alkyl, in the context of the definition of $R_1$, and also $NH_2$ or —R—$NH_2$ where R is alkyl, in the context of the definition of $R_2$ and $R_3$.

The term "glycerol type polyol", occasionally abbreviated to "glycerol", means any polyol comprising the motif —CH(OH)—$CH_2OH$. These diols may have the formula (II)

in which $R_1$ has the meaning given above.

In accordance with a particular aspect of the invention, glycerol itself is used as the starting product and solvent. Other preferred polyols are 1,2-propanediol and ethylene glycol, diglycerol, polyglycerol, amino-propanediol and carbohydrates.

The term "carbohydrate" means a monomeric or polymeric sugar such as glucose, fructose or saccharose, cited by way of non-limiting examples, and more generally mono- and polysaccharides.

In the first variation, the reaction medium for carrying out carbonation of the glycerol type polyol essentially comprises said polyol, a carbonate selected from diethyl carbonate, dimethyl carbonate, ethylene carbonate and propylene carbonate, and at least one basic catalyst, in a solvent medium.

One of the advantages of the method of the invention results from the fact that the glycerol type polyol or the glycerol may be used as a solvent in the reaction medium. However, a solvent other than glycerol or a glycerol type polyol may be used, for example ethanol, methanol, water or a mixture of solvents.

In the second implementation, the term "cyclic carbonate comprising five ring members" means cyclic carbonates with formula (IV):

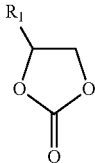

in which $R_1$ is as defined above and substitutes a cyclic carbonate comprising five ring members.

Non-limiting examples which may be cited are glycerol, propylene or ethylene carbonate or diglycerol monocarbonate, and more generally polyglycerol carbonates, including cyclic polycarbonates comprising five ring members, for example diglycerol bis-carbonate:

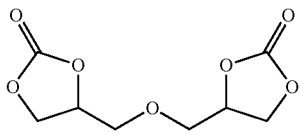 [SMILES: O=C1OCC(COCC2COC(=O)O2)O1]

The term "cyclic polycarbonates comprising five ring members" thus means cyclic carbonate compounds comprising five ring members comprising at least two cycles comprising five ring members.

The term "catalyst" in the first implementation, more precisely "basic catalyst", as used in the invention means any catalyst which is sufficiently basic to deprotonate the glycerol type polyol. In the invention, homogeneous catalysts are preferred, but heterogeneous catalysts may be employed, however.

Examples of basic catalysts which may be cited are the usual mineral bases such as KOH, NaOH, CsOH, and more generally alkali and alkaline-earth hydroxides, ammonium hydroxides, or still more generally $R_4N^+OH^-$, where $R_4$ represents a saturated $C_1$-$C_{22}$ alkyl radical. Further basic catalysts which may be cited are a rehydrated hydrotalcite or a basic ionic liquid, i.e. capable of deprotonating the glycerol type polyol, for example carrying a hydroxy group as the counter-anion such as methylbutyllimidazolinium hydroxide, or the usual highly basic polymer resins such as those sold with the trade name "Amberlyst" "A26OH" or "A26CO$_3$" by Rohm & Haas; "A26OH" is preferred. In accordance with a preferred aspect of the invention, sodium hydroxide, KOH, CsOH, ammonium hydroxide NH$_4$O, or tetramethyl ammonium hydroxide is used.

In accordance with the invention, the quantity of catalyst may be in the range 0.2% to 20% molar, preferably in the range 0.5% to 10% molar. More preferably, the basic catalyst is used in an amount of approximately 2% molar. Beyond 10% molar, in certain cases, secondary products appear during the reaction of the glycerol carbonate with the amine and the CS$_2$.

The time necessary for the carbonation reaction varies depending on the starting products and the other reaction conditions; it may be from 2 minutes to approximately 2 hours, preferably in the range 30 min to 90 min, more preferably approximately 60 min. In the first implementation, the carbonate is not isolated. It is a one-pot reaction.

The temperature of the reaction medium may be from ambient temperature (20° C.) to 200° C., depending on the nature of the reagents. In the presence of ethyl carbonate, it is preferably 100° C. to 150° C., more preferably 120° C. to 140° C., with a preference for approximately 130° C.

Following carbonation of the polyol, the intermediate glycerol carbonate is preferably reacted directly with the amine and the CS$_2$. In accordance with the invention, the primary or secondary amine and the carbon disulphide are introduced into the reaction medium.

The end of the reaction is determined, for example, by the consumption of the starting products or the maximum yield of the reaction. Any routine technique may be used to recover the GDTC, in particular liquid-liquid extraction using a suitable solvent, for example ethyl acetate. Other solvents may be used, however, such as methylisobutylketone or diethylether, or even supercritical CO$_2$.

For the separation, it is also possible to envisage distillation for sufficiently stable products, or precipitation and any other suitable means that is known to and within the ambit of the skilled person.

In accordance with the invention, a primary or secondary amine is used; any amine is suitable provided that it or its ammonium salt is soluble in the reaction medium, or that it can be rendered soluble, or that it reacts in the reaction medium, irrespective of its state. Suitable amines for use in the invention may be aromatics, such as aniline, provided that they are primary or secondary. Such amines may have formula (III) NHR$_2$R$_3$, in which R$_2$ and R$_3$ have the meanings given above.

In accordance with a particularly preferred aspect of the invention, the amines used are secondary amines. In accordance with another particularly aspect of the invention, the preferred amines are those in which R$_2$ and R$_3$ represent a linear or branched C$_1$-C$_{22}$ alkyl chain. In accordance with a particular aspect, R$_2$ and R$_3$ are identical.

Examples of preferred amines for use in the invention that may be cited are C$_1$ to C$_{22}$ alkylamines or dialkylamines, in particular diethylamine, dimethylamine, dipropylamine, diisopropylamine, diethanolamine, piperidine, for example, as well as aniline.

Depending on the reaction conditions and the products used, the step for formation of GDTC from the introduction of the amine may be from 1 to 48 hours, in particular in the range 3 to 24 hours. This reaction may in particular last approximately 15 hours.

Depending on the reagents used, the temperature may be in the range 10° C. to 100° C., for example in the range 25° C. to 80° C., with a preference for a temperature of the order of 60° C.

Regarding stoichiometry, quasi-stoichiometric nitrogen/sulphur conditions are preferred. However, the ratio of the polyol to the carbonate may be from 1 to 10, preferably 5, and the ratio of the polyol to the amine may be from 1 to 10, preferably 5, and the ratio of the polyol to CS$_2$ may be from 1 to 10, preferably 5.

In the particular case of glycerol itself, the invention offers the possibility of synthesizing glycerol dithiocarbamates in a single step directly from glycerol as the starting material source. This method involves four chemical reagents (glycerol, diethyl carbonate, CS$_2$ and a primary or secondary amine), which react together to produce glycerol dithiocarbamates, Scheme 4 below shows a mechanism for the formation of the glycerol dithiocarbamate, based on the in situ formation of glycerol carbonate.

Scheme 4

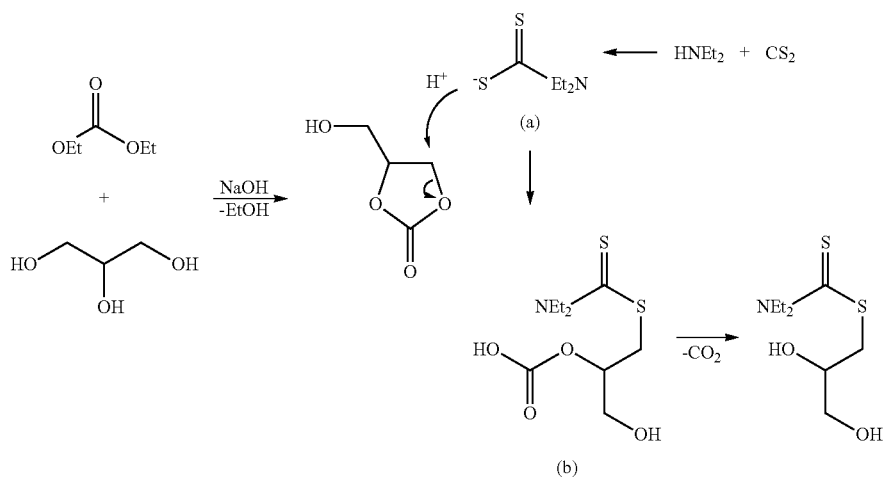

The first step is the formation of glycerol carbonate between the diethyl carbonate and the glycerol (reaction catalysed by NaOH). The $CS_2$ and the amine react together to form a dithiocarbamic acid (a) which will then add to the glycerol carbonate to generate the entity (b). This entity (b), which is unstable, is decarboxylated to produce glycerol dithiocarbamate.

In contrast to the usual chemical methods involving glycerol, this synthesis is not only chemoselective but is also regioselective. This remarkable selectivity of the method derives from the formation of glycerol carbonate as the reaction intermediate. The presence of a —$CH_2OH$ group on the glycerol carbonate in fact induces major steric hindrance, which is responsible for the high selectivity of this method.

The by-product, which is ethanol, is released during the reaction and is easily eliminated from the reaction medium, for example by distillation, then recovered and recycled. Further, the homogeneous catalyst used, namely NaOH, is in routine use in the industry and can be recycled at least 6 times without noticeable loss of activity.

In addition, from the point of view of industrial feasibility, scaling up the method has been carried out without difficulty.

Thus, it has been shown to be possible to carry out the method of the invention on a large scale, as will become apparent from the examples.

EXAMPLES

Example 1

Synthesis

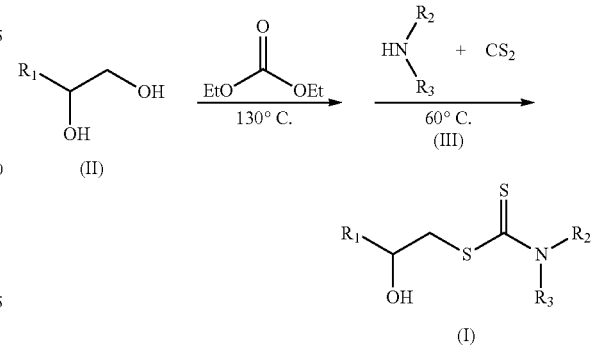

Using the following general operating procedure:
The polyol (84.5 mmole) was mixed with 16.9 mmole of diethyl carbonate in the presence of 2% molar of NaOH; during this step the ethanol was continuously distilled and recovered. After 1 hour of reaction at 130° C., 19.9 mmole of $CS_2$ and 16.9 mmole of amine were added to the medium which was stirred, at 60° C., for the whole period H.

TABLE 1

| Compound | $R_1$ polyol | $R_2/R_3$ Amine (*) | Period H (h) | Product | Isolated yield (%) |
|---|---|---|---|---|---|
| 1 | —$CH_2OH$ | —Et | 15 | ![structure] | 75 |

TABLE 1-continued

| Compound | R₁ polyol | R₂/R₃ Amine (*) | Period H (h) | Product | Isolated yield (%) |
|---|---|---|---|---|---|
| 2 | —CH₂OH | —iPr | 24 | HO-CH₂-CH(OH)-CH₂-S-C(=S)-N$^i$Pr₂ | 75 |
| 3 | —CH₂OH | —(CH₂)₅* | 24 | HO-CH₂-CH(OH)-CH₂-S-C(=S)-N(piperidine) | 70 |
| 4 | —CH₂OH | —CH₂OH | 24 | HO-CH₂-CH(OH)-CH₂-S-C(=S)-N(CH₂OH)₂ | 60 |
| 5 | —CH₂OH | —nBu | 24 | HO-CH₂-CH(OH)-CH₂-S-C(=S)-N(Bu)₂ | 63 |
| 6 | —CH₃ | —Et | 24 | CH₃-CH(OH)-CH₂-S-C(=S)-NEt₂ | 75 |
| 7 | —CH₃ | —(CH₂)₅* | 24 | H₃C-CH(OH)-CH₂-S-C(=S)-N(piperidine) | 71 |
| 8 | —CH₃ | —iPr | 24 | H₃C-CH(OH)-CH₂-S-C(=S)-N(iPr)₂ | 55 |
| 9 | —H | —Et | 24 | HO-CH₂-CH₂-S-C(=S)-NEt₂ | 81 |
| 10 | —H | —iPr | 24 | HO-CH₂-CH₂-S-C(=S)-N(iPr)₂ | 69 |
| 12 | —CH₂OH | —nOc* | 24 | nOc-N(nOc)-C(=S)-S-CH₂-CH(OH)-CH₂OH | 55 |

R₂ = R₃ or (*) —NR₂/R₃ = cycloamino

At the end of the indicated period H, the corresponding glycerol dithiocarbamate was obtained in the yield indicated in Table 1 above.

Ethylene glycerol and 1,2-propandiol were successfully used in place of glycerol, resulting in the corresponding dithiocarbamates (compounds 6 to 10 and 12).

Various amines were used successfully, resulting in the corresponding glycerol dithiocarbamates.

Example 2

2,3-dihydroxypropyl Diethyldithiocarbamate
(Compound 1)

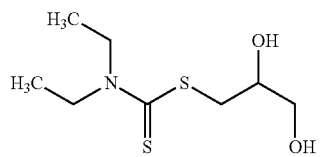

(yellow-brown oil in a mixture of ethyl acetate/heptane=3/7)

$^1$H NMR δ 1.27 (t, J=7.1 Hz, 3H), 1.28 (t, J=7.1 Hz, 3H), 2.84 (s, 1H), 3.37 (s, 1H), 3.51 (dd, J=14.5 Hz, J=6.5 Hz, 1H), 3.75 (q, J=7.2 Hz, 2H), 3.78 (t, J=7.1 Hz, 2H), 4.02 (t, J=7.1 Hz, 2H);

$^{13}$C NMR δ 11.3, 12.2, 40.8, 46.3, 48.9, 64.9, 69.8, 194.6 10.2, 10.4, 30.8, 31.0, 61.1, 62.4, 64.0, 64.2, 70.1, 70.2, 70.9, 71.1, 82.8, 84.5, 84.6, 126.7, 126.8, 127.6, 127.8, 128.4, 128.5, 141.9, 142.4.

IR (pure) 3365, 2975, 2932, 2873, 1631, 1488, 1442, 1416, 1379, 1354, 1300, 1268, 1204, 1142, 1090, 1067, 1005, 981, 915, 880, 832, 776 cm$^{-1}$;

LC.MS: [M+Na$^+$]: m/z=246

Example 3

2,3-dihydroxypropyl piperidine-1-carbodithioate
(Compound 3)

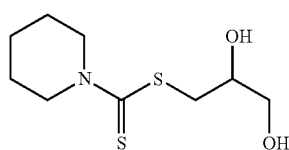

(yellow oil in a mixture of ethyl acetate/heptane=3/7)

$^1$H NMR δ 1.71 (m, 6H), 3.55 (dd, J$_1$=14 Hz, J$_2$=7 Hz, 1H), 3.6-3.75 (m, 3H), 3.9-4 (m, 3H), 4.3 (m, 2H), 3.77-3.82 (m, 1H), 4.12 (t, J=6.7 Hz, 0.9 μl), 4.30 (t, J=6.8 Hz, 0.1H), 7.21-7.34 (m, 5H);

$^{13}$C NMR δ 24.2, 25.5, 26, 39.2, 51.7, 53.8, 64.6, 71.4, 195.7;

IR (pure) 3406, 2859, 1789, 1743, 1476, 1427, 1366, 1373, 1352, 1227, 1179, 1113, 1072, 1050, 1004, 975, 892, 853, 776, 711 cm$^{-1}$;

LC.MS: [M+Na$^+$]: m/z=258

Example 4

2,3-dihydroxypropyl Dibutyldithiocarbamate
(Compound 5)

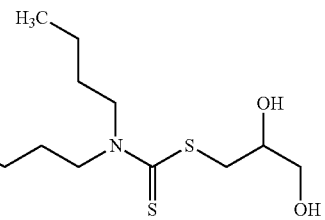

(yellow oil in a mixture of ethyl acetate/heptane=3/7)

$^1$H NMR δ 0.95 (q, 6H), 1.38 (m, 4H), 1.7 (m, 4H), 3.55 (dd, J$_1$=14 Hz, J$_2$=7 Hz, 1H), 3.6-3.7 (m, 5H), 3.95-4 (m, 3H);

IR (pure) 3363, 2958, 2931, 2872, 1788, 1642, 1484, 1456, 1413, 1367, 1289, 1249, 1217, 1184, 1144, 1091, 1030, 981, 944 930, 879, 731 cm$^{-1}$;

LC.MS: [M+Na$^+$]: m/z=302

Example 5

2-hydroxypropyl piperidine-1-carbodithioate
(Compound 7)

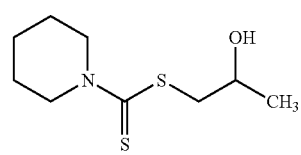

(yellow oil in a mixture of ethyl acetate/heptane=3/7)

$^1$H NMR δ 1.25 (d, J=4 Hz, 3H), 1.65 (m, 6H), 3.55 (dd, J=14 Hz, J=7 Hz, 1H), 3.65 (dd, J=14 Hz, J=4 Hz, 1H) 3.85 (m, 2H), 4 (m, 1H), 4.2 (m, 2H);

$^{13}$C NMR δ 22.52, 24.2, 25.5, 26, 44.9, 51.6, 53.5, 67.2, 195.9;

IR (pure) 3381, 2965, 2933, 2876, 1452, 1103, 1042, 727, 755, 700 cm$^{-1}$;

LC.MS: [M+Na$^+$]: m/z=228

Example 6

2-hydroxypropyl Diisopropyldithiocarbamate
(Compound 8)

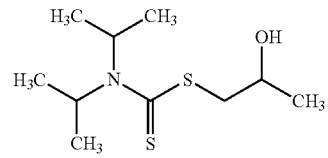

(yellow oil in a mixture of ethyl acetate/heptane=3/7)

$^1$H NMR δ 1.25 (d, 3H), 1.2-2 (m, 12H), 2.94 (m, 1H), 3.4 (m, 1H), 3.7 (m, 1H), 4.1 (m, 2H);

IR (pure) 3384, 2970, 2929, 2876, 1475, 1439, 1370, 1309, 1191, 1140, 1117, 1030, 960, 938, 896, 851, 777 cm$^{-1}$;

LC.MS: [M+Na$^+$]: m/z=258

Example 7

2-hydroxyethyl Diethyldithiocarbamate (Compound 9)

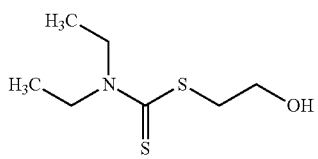

(yellow oil in a mixture of ethyl acetate/heptane=3/7)

$^1$H NMR δ 1.24 (t, J=7.2 Hz, 3H), 1.28 (t, J=7.2 Hz, 3H), 2.52 (s, 1H), 3.55 (t, J=6 Hz, 2H), 3.75 (q, J=7.2 Hz, 2H), 3.86 (t, J=6 Hz, 2H), 4.00 (q, J=7.1 Hz, 2H);

$^{13}$C NMR δ 11.6, 12.5, 39.12, 47.0, 49.9, 61.9, 195.6;

IR (pure) 3378, 2974, 2933, 2874, 1736, 1487, 1442, 1416, 1379, 1355, 1301, 1267, 1204, 1142, 1082, 1067, 1044, 1003, 980, 915, 832, 775 cm$^{-1}$;

LC.MS: [M+Na$^+$]: m/z=216

Example 8

Compound 12

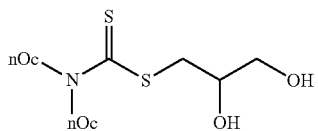

was obtained using the method of Example 1.

In addition, the synthesis was carried out on a much larger scale in order to obtain 1 kg of compound 12.

Glycerol (7.3 mole) was mixed with 14.6 mole of diethyl carbonate in the presence of 2% molar NaOH; during this step, the ethanol was continuously distilled and recovered. After 2 hours of reaction at 130° C., 7.3 mole of CS$_2$ and 7.3 mole of amine were added to the medium which was stirred at 60° C. for 72 hours. The product was then purified by column chromatography with pure heptane as the eluent.

Example 9

In order to demonstrate the possible limitation of the economic and environmental costs of the method, the catalyst (NaOH) was recycled as well as the excess glycerol used.

Figure 2:
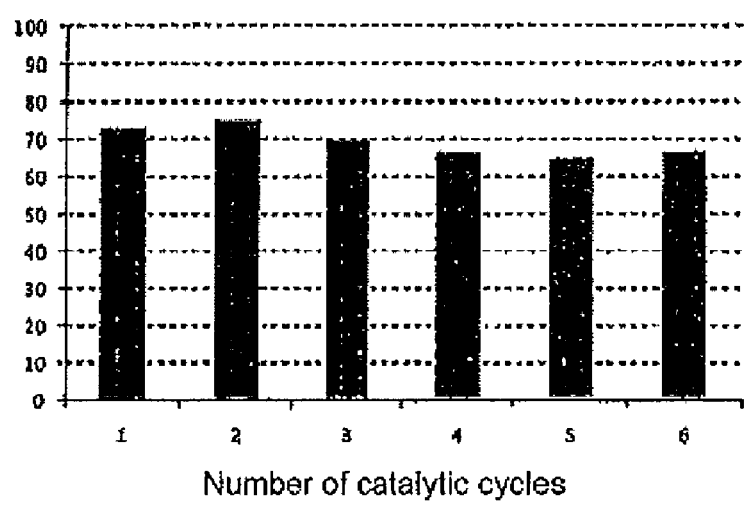
FIG. 2 represents the results of recycling the glycerol/NaOH phase in a method of the invention, in particular that of FIG. 1.

A liquid-liquid extraction was carried out to extract the glycerol dithiocarbamates from the glycerol phase with ethyl acetate. The starting products were glycerol (84.5 mmole), diethylamine (16.9 mmole), diethyl carbonate (16.9 mmole) and CS$_2$ (16.9 mmole). After only two extractions with ethyl acetate (4×30 ml), all of the glycerol dithiocarbamate had been extracted (FIG. 2).

An acid-base titration of the glycerol phase revealed that the NaOH catalyst remained entirely dissolved in the glycerol phase. The glycerol/NaOH phase was re-used. Hence, after recharging with 16.9 mmole of glycerol, diethylamine, CS$_2$ and diethyl carbonate, yields of 73% were again obtained (FIG. 2).

As can be seen in FIG. 1, the glycerol/NaOH phase could be recycled at least 6 times without any noticeable drop in yield. The ethyl acetate was also recycled after each extraction.

Example 10

The method of Example 1 was scaled up without difficulty and the glycerol dithiocarbamates of Example 1 (10-15 g) were all obtained.

Example 11

Method with cyclic carbonates comprising five ring members.

The cyclic carbonates below were reacted in ethanol at 60° C. in accordance with scheme 3, using the amines indicated; the yields given below in Table II were obtained at the end of the period H.

TABLE II

| Compound | R$_2$/R$_3$ Amine (*) | R$_1$ carbonate | Period H (h) | Product | Isol. yld. (%) |
|---|---|---|---|---|---|
| 1 | —Et | —CH$_2$OH | 15 | HO–CH$_2$–CH(OH)–CH$_2$–S–C(=S)–NEt$_2$ | 91 |
| 2 | —iPr | —CH$_2$OH | 24 | HO–CH$_2$–CH(OH)–CH$_2$–S–C(=S)–N$^i$Pr$_2$ | 85 |

TABLE II-continued
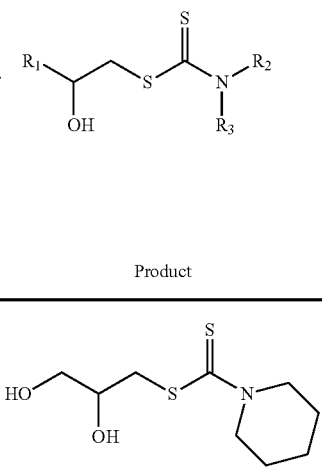
| Compound | R₂/R₃ Amine (*) | R₁ carbonate | Period H (h) | Product | Isol. yld. (%) |
|---|---|---|---|---|---|
| 3 | —(CH₂)₅* | —CH₂OH | 24 | 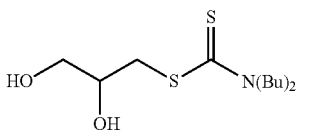 | 84 |
| 5 | —nBu | —CH₂OH | 24 | 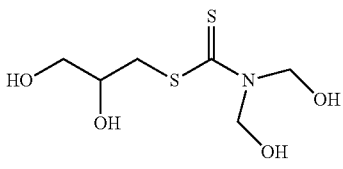 [SMILES: OCC(O)CSC(=S)N(CO)CO] | 78 |
| 4 | —CH₂OH | —CH₂OH | 24 | 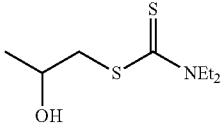 | 55 |
| 6 | —Et | —CH₃ | 24 | 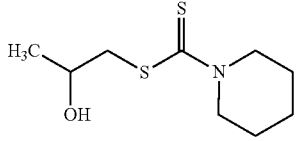 | 95 |
| 7 | —(CH₂)₅* | —CH₃ | 24 | 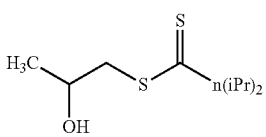 | 71 |
| 8 | —iPr | —CH₃ | 24 | 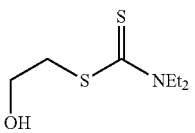 | 55 |
| 9 | —Et | —H | 24 | 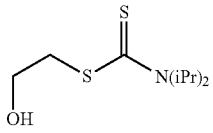 | 93 |
| 10 | —iPr | —H | 24 |  | 55 |

TABLE II-continued

R₁-substituted 1,3-dioxolan-2-one + HNR₂R₃ + CS₂ → (EtOH/60° C.) → R₁CH(OH)CH₂-S-C(=S)-NR₂R₃

| Compound | R₂/R₃ Amine (*) | R₁ carbonate | Period H (h) | Product | Isol. yld. (%) |
|---|---|---|---|---|---|
| 11 | —Et | —H₂OCH₂CHOHCH₂OH | 24 | HOCH₂CH(OH)CH₂-O-CH₂CH(OH)CH₂-S-C(=S)-N(Et)₂ | 37 |

*NR₂/R₃ = cycloamino

Example 12

The following reactions were carried out in the same manner:

R'₁R'₂N-C(=S)-S-CH₂-(1,3-dioxolan-2-one) + HNR₂R₃ + CS₂ → (60° C.) → R'₁R'₂N-C(=S)-S-CH₂-CH(OH)-CH₂-S-C(=S)-NR₂R₃

| Compound | Amine | Period (H) | Product | Isolated yield (%) |
|---|---|---|---|---|
| 13 | —Et | 24 | Et₂N-C(=S)-S-CH₂-CH(OH)-CH₂-S-C(=S)-NEt₂ | 35 |
| 14 | —nBu | 40 | (nBu)₂N-C(=S)-S-CH₂-CH(OH)-CH₂-S-C(=S)-N(nBu)₂ | 33 |
| 15 | —nOc | 48 | (nOc)₂N-C(=S)-S-CH₂-CH(OH)-CH₂-S-C(=S)-N(nOc)₂ | 29 |

Example 13

The following reactions were carried out in similar manner with two equivalents of amine and two equivalents of CS$_2$:

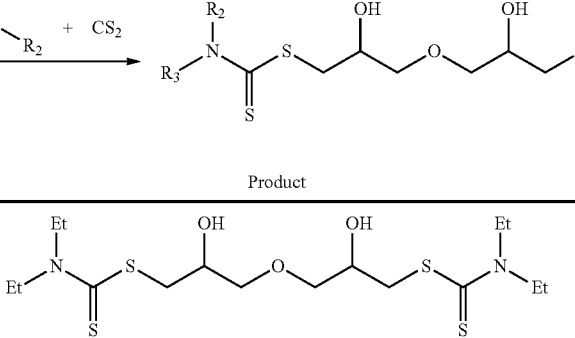

| Compound | Amine | Period (H) | Product | Isolated yield (%) |
|---|---|---|---|---|
| 16 | —Et | 24 | 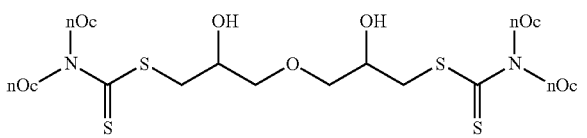 | 26 |
| 17 | —nOc | 40 | 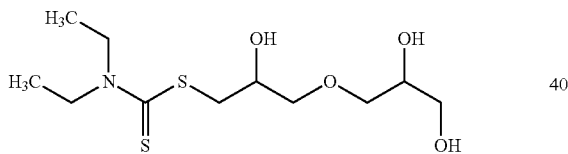 | 21 |

Example 14

3-(2,3-dihydroxypropoxy)-2-hydroxypropyl Diethyldithiocarbamate (Compound 11)

The compound of the heading was obtained using the method of Example 11:

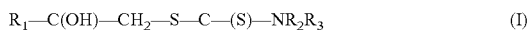

(yellow oil) 1H NMR δδ 1.20 (t, J=7.1 Hz, 3H), 1.25 (t, J=7.1 Hz, 3H), 3.3-3.5 (m, 6H), 3.55 (q, J=6.5 Hz, 1H), 3.7 (m, 1H), 335 (q, J=7.2 Hz, 2H), 3.82 (m, 1H), 3.95 (q, J=7.2 Hz, 2H), 4.05 (m, 1H); 13C NMR δ 11.3, 14, 46.4, 49, 59.7, 63, 70.4, 72.9, 74.4, 82.1, 194.3

REFERENCES

1. Rafin, E. Veignie, M. Sancholle, D. Postel, C. Len, P. Villa, G. Ronco, *J. Agric. Food Chem.*, 2000, 48, 5283;
2. C. Len, D. Postel, G. Ronco, P. Villa, C. Goubert, E. Jeufrault, B. Mathon, H. Simon, *J. Agric. Food Chem.*, 1997, 45, 3;
3. C. Len, A.-S, Boulogne-Merlot, D. Postel, G. Ronco, P, Villa, C. Goubert, E. Jeufrault, B, Mathon, H. Simon, *J. Agric. Food Chem.*, 1996, 44, 2856;
4. C. Len, D. Postel, B. Meddah, P. Villa, G. Ronco, *Phosphorus, Sulphur and Silicon*, 2001, 173, 59;
5. C. Len, D. Postel, G. Ronco, P. Villa, *J. Carbohydr. Chem.*, 1997, 16(7), 1029;
6. C. Len, D. Postel, G. Ronco, P. Villa, *Phosphorus, Sulphur and Silicon*, 1998, 133, 41.

The invention claimed is:

1. A method for the preparation of a glycerol dithiocarbamate (GDTC) of formula $$R_1-C(OH)-CH_2-S-C-(S)-NR_2R_3 \quad (I)$$

or $$R'_1R'_2-N-C(S)-S-CH_2-CH(OH)-CH_2-S-C(S)-NR_2R_3 \quad (I')$$

or $$R_2R_3-N-C(S)-S-CH_2-CH(OH)-CH_2-O-CH_2-CH(OH)-CH_2-S-C(S)-NR_2R_3 \quad (I'')$$

in which

R$_1$ represents H; a linear or branched C$_1$-C$_{22}$ alkyl radical or a C$_3$-C$_{16}$ cyclo-alkyl radical optionally substituted with one or more hydroxy, —O-alkyl, thiohydroxy or —S-alkyl groups, the chain of the alkyl radical optionally being interrupted by one or more O, N or S heteroatoms; a linear or branched C$_2$-C$_{22}$ alkenyl radical mono- or poly-unsaturated; a C$_2$-C$_6$ alkynyl radical; a C$_6$-C$_{10}$ aryl radical; or a C$_7$ to C$_{22}$ arylalkyl radical; and R$_2$ and R$_3$, independently of each other, represent H; a linear or branched C$_1$-C$_{22}$ alkyl radical or a C$_3$-C$_{16}$ cyclo-alkyl radical optionally substituted with one or more hydroxy, —O-alkyl, thiohydroxy or —S-alkyl groups, the chain of the alkyl radical optionally being interrupted by one or more O, N or S heteroatoms; a linear or branched, mono- or poly-unsaturated C$_2$-C$_{22}$ alkenyl radical; a C$_2$-C$_6$ alkynyl radical; a C$_6$-C$_{16}$ aryl radical; or a C$_7$ to C$_{22}$ arylalkyl radical; or R$_2$ and R$_3$ together with the nitrogen atom to which they are bonded form a cycloamino group;

R'$_1$ and R'$_2$ have the same meanings as R$_2$ and R$_3$, wherein said method comprises
implementing a reaction medium with a carbon disulphide $CS_2$ and a primary or secondary amine $NHR_2R_3$ wherein $R_2$ and $R_3$ are as defined above,
said reaction medium comprising
(a) a glycerol type polyol of formula $$R_1\text{—CH(OH)—CH}_2\text{OH} \qquad (II)$$

in which $R_1$ has the same meanings as above and a carbonate selected from the group consisting of diethyl carbonate, dimethyl carbonate, ethylene carbonate and propylene carbonate in the presence of a basic catalyst, or (b) a cyclic carbonate comprising five ring members having the following formula (IV):

(IV)

wherein $R_1$ has the same meanings as above, or (c) a cyclic carbonate comprising five ring members of formula in which $R'_1$ and $R'_2$, independently of each other, represent H; a linear or branched $C_1$-$C_{22}$ alkyl radical or a $C_3$-$C_{16}$ cyclo-alkyl radical optionally substituted with one or more hydroxy, —O-alkyl, thiohydroxy or —S-alkyl groups, the chain of the alkyl radical optionally being interrupted by one or more O, N or S heteroatoms; a linear or branched, mono- or poly-unsaturated $C_2$-$C_{22}$ alkenyl radical; a $C_2$-$C_6$ alkynyl radical; a $C_6$-$C_{16}$ aryl radical; or a $C_7$ to $C_{22}$ arylalkyl radical; or $R'_1$ and $R'_2$ together with the nitrogen atom to which they are bonded form a cycloamino group; or (d) a cyclic polycarbonate comprising five ring members; and recovering the formed GDTC.

2. The method according to claim 1, wherein said reaction medium comprises a glycerol type polyol of formula (II):

(II)

before supplementing with said primary or secondary amine.

3. The method according to claim 1, wherein said reaction medium comprises a carbonate of formula (IV):

(IV)

4. The method according to claim 1, wherein the GDTC has formula (I) $R_1\text{—C(OH)—CH}_2\text{—S—C—(S)—NR}_2R_3$.

5. The method according to claim 1, wherein said secondary amine is a dialkylamine.

6. The method according to claim 1, wherein said amine is a member selected from the group consisting of diethylamine, dimethylamine, dipropylamine, diisopropylamine, piperidine, diethanolamine and aniline.

7. The method according to claim 1, wherein said carbonate is diethyl carbonate.

8. The method according to claim 1, wherein said glycerol type polyol is selected from glycerol, 1,2-propanediol and ethylene glycol.

9. The method according to claim 1, wherein said catalyst is a member selected from the group consisting of KOH, NaOH, CsOH, ammonium or tetraalkylammonium hydroxide, "Amberlyst A26OH", a rehydrated hydrotalcite and a basic ionic liquid.

10. The method according to claim 1, wherein the quantity of catalyst is in the range 0.2% to 20% molar.

11. The method according to claim 1, wherein said cyclic carbonate comprising five ring members is a member selected from the group consisting of glycerol carbonate, propylene carbonate, ethylene carbonate, glycerol monocarbonate and diglycerol bis-carbonate.

12. The method according to claim 1, wherein said reaction medium comprises a glycerol type polyol as the solvent.

13. The method according to claim 12, wherein said glycerol type polyol is a member selected from the group consisting of glycerol, 1,-2-propanediols, ethylene glycol, diglycerol, polyglycerol and amino-propanediol.

14. The method of claim 9, wherein said catalyst is NaOH.

15. The method of claim 1, wherein said range is 0.5% to 10% molar.

16. The method of claim 1, wherein the quantity of catalyst is approximately 2% molar.

17. The method of claim 1, wherein $R_1$ is $CH_2OH$.

18. The method of claim 1, wherein $R_2$ and $R_3$, independently of each other, represent a linear or branched $C_1$-$C_{12}$ alkyl radical.

19. The method of claim 1, wherein $R_2$ and $R_3$, independently of each other, represent a linear or branched $C_1$-$C_8$ alkyl radical.

* * * * *